United States Patent [19]

Imbach et al.

[11] Patent Number: 4,659,698

[45] Date of Patent: Apr. 21, 1987

[54] PHARMACEUTICAL COMPOSITIONS BASED ON XYLOSIDES AND LYXOSIDES OF PURINE AND PYRIMIDINE BASES USED IN A METHOD OF TREATING VIRUSES

[75] Inventors: Jean-Louis Imbach, 1108, rue de Las Sorbes, 34000 Montpellier; Gilles Gosselin, Montpellier; Jean De Rudder, Versailles, all of France

[73] Assignees: Synthelabo, Paris; Jean-Louis Imbach, Montpellier, both of France

[21] Appl. No.: 734,846

[22] Filed: May 16, 1985

Related U.S. Application Data

[63] Continuation of Ser. No. 503,560, Jun. 13, 1983, abandoned.

[30] Foreign Application Priority Data

Jun. 14, 1982 [FR] France ................................ 82 10289

[51] Int. Cl.$^4$ .............................................. A61K 31/70
[52] U.S. Cl. ......................................... 514/49; 514/45; 514/46; 514/50; 536/23; 536/24; 536/25
[58] Field of Search .................... 514/46, 49, 50, 45; 536/26, 23, 24

[56] References Cited

PUBLICATIONS

Eppstein et al, Nature vol. 302, Apr. 21, 1983, pp. 723–724.

Chem. Pharm. Bull. 19, 538 (1971).

*Primary Examiner*—Johnnie R. Brown
*Attorney, Agent, or Firm*—Wegner & Bretschneider

[57] ABSTRACT

Pharmaceutical compositions which contain a xyloside or a lyxoside of a purine or pyrimidine base selected from the following compounds:
1-($\beta$-D-xylofuranosyl)-cytosine, 1-($\beta$-D-xylofuranosyl)-thymine, 9-($\alpha$-D-xylofuranosyl)-adenine, 9-($\alpha$-D-xylofuranosyl)-guanine, 1-($\alpha$-D-xylofuranosyl)-cytosine, 1-($\alpha$-D-xylofuranosyl)-thymine, 1-($\beta$-D-lyxofuranosyl)-adenine, 9-($\beta$-D-lyxofuranosyl)-guanine, 1-($\beta$-D-lyxofuranosyl)-cytosine, 1-($\beta$-D-lyxofuranosyl)-thymine, 9-($\alpha$-D-lyxofuranosyl)-adenine, 1-($\alpha$-D-lyxofuranosyl)-guanine, 1-($\alpha$-D-lyxofuranosyl)-cytosine and 1-($\alpha$-D-lyxofuranosyl)-thymine, have been found to be useful in therapy for treating various viral diseases.

6 Claims, No Drawings

PHARMACEUTICAL COMPOSITIONS BASED ON XYLOSIDES AND LYXOSIDES OF PURINE AND PYRIMIDINE BASES USED IN A METHOD OF TREATING VIRUSES

DESCRIPTION

This application is a continuation of Ser. No. 503,560, filed June 13, 1983, now abandoned.

The present invention relates to pharmaceutical compositions based on xylosides and lyxosides of purine and pyrimidine bases.

The medicaments of the invention are active, in particular, against DNA (i.e. deoxyribonucleic acid) viruses such as herpes, vaccinia and adeno viruses.

The xylosides and lyxosides of purine and pyrimidine bases used according to the invention are as follows:

1-(β-D-xylofuranosyl)-cytosine, 1-(β-D-xylofuranosyl)-thymine, 9-(α-D-xylofuranosyl)-adenine, 9-(α-D-xylofuranosyl)-guanine, 1-(α-D-xylofuranosyl)-cytosine, 1-(α-D-xylofuranosyl)-thymine, 9-(β-D-lyxofuranosyl)-adenine, 9-(β-D-lyxofuranosyl)-guanine, 1-(β-D-lyxofuranosyl)-cytosine, 1-(β-D-lyxofuranosyl)-thymine, 9-(α-D-lyxofuranosyl)-adenine, 9-(α-D-lyxofuranosyl)-guanine, 1-(α-D-lyxofuranosyl)-cytosine and 1-(α-D-lyxofuranosyl)-thymine.

The majority of these compounds are known substances which have already been described in the literature.

The β-D-xylofuranosyl-bases correspond to the following general formula:

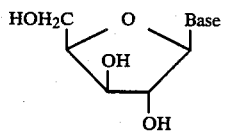

The α-D-xylofuranosyl-bases correspond to the following general formula:

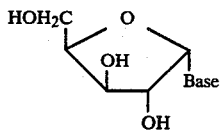

The β-D-lyxofuranosyl-bases correspond to the following general formula:

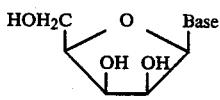

The α-D-lyxofuranosyl-bases correspond to the following general formula:

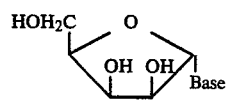

1-(β-D-Xylofuranosyl)-cytosine of the formula:

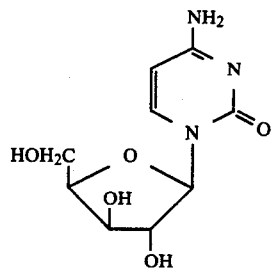

is a substance which is already known and described by J. J. Fox, et al. (JACS 79, 5060, (1957)) and V. Brodbeck et al. (J. Org. Chem. 35, 3552, (1970)).

1-(β-D-xylofuranosyl)-thymine of the formula:

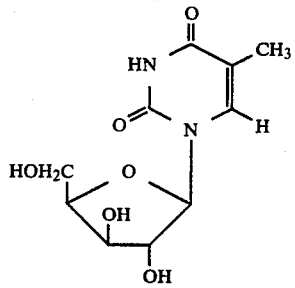

has been described by J. J. Fox et al. (JACS, 78, 2117, (1956)); JACS, 80, 5155, (1958)) and E. M. Kaz'mina et al. (Chem. Abs. 80, 121250s (1974); Chem. Abst. 89, 180287t (1978)).

9-(α-D-Xylofuranosyl)-adenine has been described by A. Magnani et al. (Carbohyd. Res. 28, 158, (1973)), W. W. Lee et al. (Chem. Ind. London, 2007, (1963)) and M. Ikehara et al. (Tetrahedron Lett., 4707, (1968)); Chem. Pharm. Bull. 19, 538, (1971)).

9-(α-D-Xylofuranosyl)-guanine has been described by Suzaki et al. (Chem. Pharm. Bull. 1970, 18, 172) and W. W. Lee et al. (J. Org. Chem. 36, 842, (1971)).

1-(α-D-Xylofuranosyl)-cytosine has been described by Post et al. in Can. J. Chem. 59 (2), 238, (1981) and I. Ekiel et al. (J. Carbohyd. Nucleosides Nucleotides, 8, 279, (1981)).

1-(α-D-Xylofuranosyl)-thymine, which is not described in the literature, has a melting point of 196°–197° C. and is obtained from 1-(α-D-xylofuranosyl)-uracil, the latter having been described by A. Hols (Collect. Czech. Chem. Comm., 38, 428, (1973)).

9-(β-D-lyxofuranosyl)adenine of the formula:

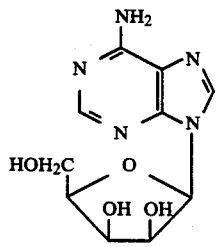

has been described by E. J. Reist (Chemistry and Industry, 1561, (1965); J. Org. Chem. 32, 169 (1967)).

9-(β-D-lyxofuranosyl)-guanine of the formula:

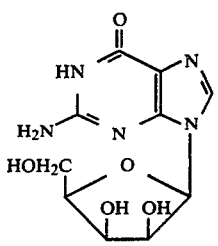

has hitherto never been described in the literature.

1-(α-D-Lyxofuranosyl)-cytosine of the formula:

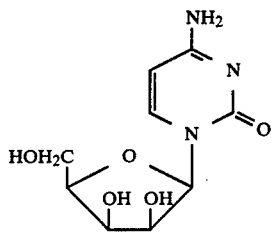

has been described by T. Kanai et al. (Chem. Pharm. Bull. 16, (9) 1848, (1968)) and J. J. Fox et al. (JACS, 83, 1889 (1961); J. Org. Chem. 27, 1477 (1962)).

1-(β-D-Lyxofuranosyl)-thymine of the formula:

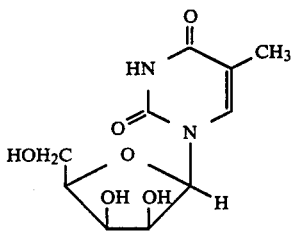

has been described by J. J. Fox et al. (JACS, 80, 5155 (1958)) and T. Nishimura et al. (Chem. Pharm. Bull. 12, 803 (1965)).

9-(α-D-Lyxofuranosyl)-adenine has been described by P. Kohn et al. (J. Org. Chem., 32, 4076 (1967)).

1-(α-D-Lyxofuranosyl)-thymine has been described by M. Smrz et al. (Collect. Czech. Chem. Comm., 33, 3803, 1968)) at T. Nishimura et al. (Chem. Pharm. Bull. 13, 803 (1965)).

9-(α-D-Lyxofuranosyl)-guanine has hitherto never been described in the literature. Its preparation is described in following Example 2. Its melting point is 246° C. (decomposition).

1-(α-D-Lyxofuranosyl)-cytosine has hitherto never been described in the literature. Its melting point is 198°–200° C. Its preparation is described in following Example 3.

The (β-D-xylosides and α-D-lyxosides were prepared by condensation methods chosen individually according to the reactivity of the aglycone.

The α-D-xylosides were synthesised according to two stereospecific total synthesis approaches.

The β-D-lyxosides were prepared by chemical conversion of the corresponding β-D-xylosides.

The preparation of three of the compounds used according to the invention is described in the examples which follow.

The analyses and the UV, mass and NMR spectra confirmed the structures of the compounds.

EXAMPLE 1

1-(β-D-Xylofuranosyl)-cytosine

One equivalent of cytosine is condensed with one equivalent of 1-O-acetyl-2,3,5-tri-O-benzoyl-α-D-xylofuranose at ambient temperature, in anhydrous acetonitrile, in the presence of tin tetrachloride, $SnCl_4$ (2 equivalents); the compound obtained is purified by chromatography on a silica column and debenzoylated using a methnol solution saturated with ammonia gas. This gives 1-(β-D-xylofuranosyl)-cytosine.

Melting point 240°–242° C. (decomposition).

EXAMPLE 2

9-(α-D-Lyxofuranosyl)-guanine 1.15 equivalents of silylated $N^2$-acetylguanine are reacted with one equivalent of 1,2,3,5-tetra-O-acetyl-D-lyxofuranose in anhydrous 1,2-dichloroethane, in the presence of 1.2 equivalents of trimethylsilyl triflate $[F_3CSO_2Si(CH_3)_3]$. The reaction mixture is heated under reflux for one hour. The resulting solution is diluted with dichloroethane and the organic phase is extracted successively with iced water, with a saturated aqueous solution of sodium bicarbonate and with water. The organic phases are dried over sodium sulphate and filtered and the filtrate is evaporated to dryness.

Analysis of the resulting foam by thin layer chromatography shows mainly two distinct spots, corresponding to two nucleoside derivatives.

These were isolated and characterised after chromatography on a silica column; they correspond respectively, in the order to which they are eluted, to $N^2$-acetyl-2',3',5'-tri-O-acetyl-7-(α-D-lyxofuranosyl)-guanine and $N^2$-acetyl-2',3',5'-tri-O-acetyl-9-(α-D-lyxofuranosyl)-guanine.

The latter compound is then dissolved in a 0.1N methanolic solution of sodium methoxide and the resulting solution is heated under reflux for forty-five minutes. After cooling and evaporation to dryness, the residue is taken up in water and the mixture is neutralised with Dowex 50 resin, pyridinium form. After the resin has been filtered off, the 9-(α-D-lyxofuranosyl)-guanine is crystallised from water.

EXAMPLE 3

1-(α-D-lyxofuranosyl)-cytosine

One equivalent of cytosine is condensed with one equivalent of 1,2,3,5-tetra-O-acetyl-D-lyxofuranose in anhydrous acetonitrile, under reflux, for one hour thirty minutes, in the presence of two equivalents of tin tetrachloride.

After the reaction mixture has been treated with sodium bicarbonate and water, the 2',3',5'-tri-O-acetyl-1-(α-D-lyxofuranosyl)-cytosine obtained is purified by chromatography on a silica column. This compound is then deacetylated by means of a methanol solution saturated with ammonia gas.

1-(α-D-Lyxofuranosyl)-cytosine thus obtained is then purified by column chromatography and subsequently crystallised from ethanol.

Melting point 198°–200° C.

The compounds used according to the invention possess virostatic properties and were studied in vitro under the following conditions:

The studies were carried out on HeLa cells cultivated in a medium consisting of Earle's solution treated with 0.5% of lactalbumin hydrolysate, 0.1% of yeast extract and 5% of calf serum, the medium having been filtered and deactivated for thirty minutes at 56° C. The culture is carried out in fixed tubes containing 1 ml of this medium. When the cell layers are well developed, the culture medium is removed and 0.1 ml of a suspension of herpes virus in Hanks liquid, at a sufficient concentration to contain from 10 to 50 IDTC$_{50}$ (50% infectious dose in tissue culture) per cell, is introduced into each tube. Absorption is allowed to proceed at 37° C. for two hours. The supernatant is removed and the cell layer is washed with a buffered isotonic solution. 1 ml of the sustaining medium (similar medium, but containing 2.5% of serum), to which the substance to be tested has been added beforehand at a concentration of $3.3 \times 10^{-4}$M, is then introduced. Control cultures, which do not contain active compound and are inoculated with the herpes virus under the same conditions, are also prepared. All the tubes are incubated in an oven at 35° C. When the controls show a complete cytopathogenic effect, the infectious virus is determined in all the tubes by the method of establishing the 50% limiting dilution. A difference of 3 to 5 base-10 logarithmic units is found between the infectious titers of the treated tubes and the control tubes, which shows complete blockage of virus production in the treated tubes.

Two of the compounds mentioned at the beginning of this specification, namely 1-(β-D-xylofuranosyl)-cytosine and 9-(α-D-lyxofuranosyl)-adenine, were more particularly studied with respect to the activity on herpes virus (H. hominis type 1) in HeLa cell cultures. In the control batch, the titer of the virus is about $10^{6.5}$ (IDTC$_{50}$/ml).

When the substance to be tested is introduced, the titer of the virus decreases and is respectively $10^{3.6}$ and $10^{2.5}$ (IDTC$_{50}$/ml).

The toxicity of the compounds with respect to normal cells in culture is very low.

Because of their virostatic properties and their low toxicity towards cells, the purine and pyrimidine xylosides and lyxosides mentioned at the beginning of this specification are substances which are useful in therapy for treating various viral diseases such as herpetic keratitis, skin herpes and zona, and also the diseases caused by poxviruses and adenoviruses.

The pharmaceutical compositions of the invention can be liquid or solid and can be presented in the form of solutions, eye lotions, salves, ointments and the like.

They are prepared by the customary methods. The active principle can be incorporated into pharmaceutical excipients normally used in such compositions and chosen according to the galenical form to be produced. These excipients can consist of aqueous or non-aqueous solvents, stabilisers, wetting agents, vaselines, lanolins, polyethylene glycols and polyhydroxyethylated or non-polyhydroxyethylated fatty acid esters of sorbitan.

The concentration of active principle in the pharmaceutical preparations produced in this way can vary according to the seriousness of the particular case and the intended method of use: for example, it can be between 0.1% and 5%.

We claim:

1. A method for the treatment of viral diseases which comprises administering to an animal suffering from a viral disease a viral disease treating effective amount of 1-(β-D-xylofuranosyl)-cytosine.

2. A method for the treatment of viral diseases which comprises administering to an animal suffering from a viral disease a viral disease-treating effective amount of 9-(α-D-Lyxofuranosyl)-adenine.

3. A pharmaceutical composition for treating an H. hominis type 1 virus comprising an H. hominis type 1 virus-treating effective amount of 1-(β-D-xylofuranosyl)-cytosine and a pharmaceutically acceptable carrier therefor.

4. A pharmaceutical composition for treating an H. hominis type 1 virus comprising an H. hominis type 1 virus-treating effective amount of 9-(α-D-Lyxofuranosyl)-adenine and a pharmaceutically acceptable carrier therefor.

5. 9-(α-D-Lyxofuranosyl)-guanine.

6. 1-(α-D-Lyxofuranosyl)-cytosine.

* * * * *